United States Patent
Min et al.

(10) Patent No.: US 9,381,357 B2
(45) Date of Patent: Jul. 5, 2016

(54) METHODS AND SYSTEMS FOR MONITORING ELECTRICAL STIMULATION USING PADDLE LEAD

(71) Applicant: PACESETTER, INC., Sylmar, CA (US)

(72) Inventors: Xiaoyi Min, Camarillo, CA (US);
Timothy A. Fayram, Gilroy, CA (US);
Brad Maruca, Fairview, TX (US); Enri Zhulati, Fort Worth, TX (US); Kyle Pulley, Plano, TX (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 14/252,546

(22) Filed: Apr. 14, 2014

(65) Prior Publication Data
US 2015/0290461 A1   Oct. 15, 2015

(51) Int. Cl.
*A61N 1/36* (2006.01)
*A61N 1/372* (2006.01)
*A61N 1/08* (2006.01)
*A61N 1/05* (2006.01)

(52) U.S. Cl.
CPC .......... *A61N 1/36135* (2013.01); *A61N 1/0553* (2013.01); *A61N 1/08* (2013.01); *A61N 1/37235* (2013.01)

(58) Field of Classification Search
CPC ... A61N 1/36135; A61N 1/0553; A61N 1/08; A61N 1/37235
See application file for complete search history.

(56) References Cited

U.S. PATENT DOCUMENTS

| 6,516,227 | B1 * | 2/2003 | Meadows | ............. | A61N 1/0553 607/117 |
| 2006/0224187 | A1 * | 10/2006 | Bradley | ............. | A61N 1/36071 607/2 |
| 2014/0163639 | A1 | 6/2014 | Zhu | | |

* cited by examiner

*Primary Examiner* — Rex R Holmes

(57) ABSTRACT

The present disclosure provides systems and methods for neurostimulation. The method includes applying electrical stimulation to a patient using a paddle lead that includes a plurality of electrodes, acquiring evoked response data using at least some of the plurality of electrodes, wherein the evoked response data is indicative of a patient response to the electrical stimulation, transmitting the evoked response data to a computing device, and processing the evoked response data using the computing device to facilitate monitoring the applied electrical stimulation.

17 Claims, 10 Drawing Sheets

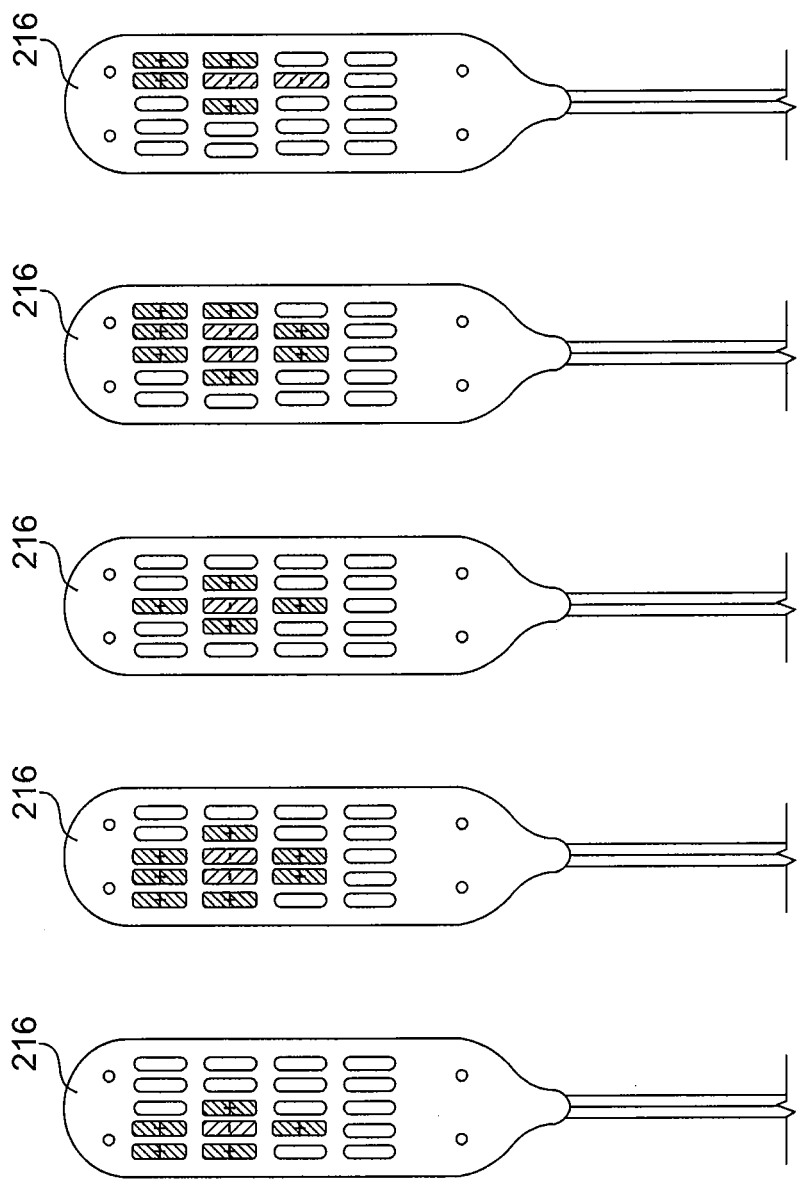

| I(mA) | LEFT | | | | | | | | RIGHT | | | | | | | |
|---|---|---|---|---|---|---|---|---|---|---|---|---|---|---|---|---|
| | L1 | L2 | L3 | L4 | L5 | S1 | S2 | S3 | S3 | S2 | S1 | L5 | L4 | L3 | L2 | L1 |
| 10.0 | x | x | x | x | x | x | x | x | | | | | | | | |
| 7.5 | | x | x | x | x | x | x | x | | | | | | | | |
| 5.0 | | | | x | x | x | | | | | | | | | | |
| 3.3 | | | | x | x | | | | | | | | | | | |

METHODS AND SYSTEMS FOR
MONITORING ELECTRICAL STIMULATION
USING PADDLE LEAD

FIELD OF THE DISCLOSURE

The present disclosure relates generally to neurostimulation methods and systems, and more particularly to monitoring electrical stimulation applied using a paddle lead.

BACKGROUND ART

Application of electrical fields to spinal nerve roots, spinal cord, and other nerve bundles for the purpose of chronic pain control has been actively practiced for some time. While a precise understanding of the interaction between applied electrical energy and the nervous tissue is not fully appreciated, application of an electrical field to spinal nervous tissue (i.e., spinal nerve roots and spinal cord bundles) can effectively mask certain types of pain transmitted from regions of the body associated with the stimulated nerve tissue. Specifically, applying electrical energy to regions of the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

Each exterior region, or each dermatome, of the human body is associated with a particular spinal nerve root at a particular longitudinal spinal position. The head and neck regions are associated with C2-C8, the back regions extend from C2-S3, the central diaphragm is associated with spinal nerve roots between C3 and C5, the upper extremities correspond to C5 and T1, the thoracic wall extends from T1 to T11, the peripheral diaphragm is between T6 and T11, the abdominal wall is associated with T6-L1, lower extremities are located from L2 to S2, and the perineum from L4 to S4. In conventional neurostimulation, when a patient experiences pain in one of these regions, a neurostimulation lead is implanted adjacent to the spinal cord at the corresponding spinal position. For example, to address chronic pain sensations that commonly focus on the lower back and lower extremities using conventional techniques, a specific energy field is typically applied to a region between vertebrae levels T8 and T12. The specific energy field often stimulates a number of nerve fibers and structures of the spinal cord. By applying energy in this manner, the patient commonly experiences paresthesia over a relatively wide region of the patient's body from the lower back to the lower extremities.

Positioning of an applied electrical field relative to a physiological midline is also important. Nerve fibers extend between the brain and a nerve root along the same side of the dorsal column that the peripheral areas the fibers represent. Pain that is concentrated on only one side of the body is "unilateral" in nature. To address unilateral pain, electrical energy is applied to neural structures on the side of a dorsal column that directly corresponds to a side of the body subject to pain. Pain that is present on both sides of a patient is "bilateral". Accordingly, bilateral pain is addressed through application of electrical energy along both sides of the column and/or along a patient's physiological midline.

Percutaneous leads and laminotomy leads are the two most common types of lead designs that provide conductors to deliver stimulation pulses from an implantable pulse generator (IPG) to distal electrodes adjacent to the pertinent nerve tissue. Example commercially available stimulation leads include the QUATTRODE™, OCTRODE™, AXXESS™, LAMITRODE™, TRIPOLE™, EXCLAIM™, and PENTA™ stimulation leads from St. Jude Medical, Inc. As shown in FIG. 1A, a conventional percutaneous lead 100 includes electrodes 101 that substantially conform to the body of the body portion of the lead. Due to the relatively small profile of percutaneous leads, percutaneous leads are typically positioned above the dura layer through the use of a Touhy-like needle. Specifically, the Touhy-like needle is passed through the skin, between desired vertebrae to open above the dura layer for the insertion of the percutaneous lead.

As shown in FIG. 1B, a conventional laminotomy or paddle lead 150 has a paddle configuration and typically possesses a plurality of electrodes 151 (commonly, two, four, eight, or sixteen) arranged in columns. Due to their dimensions and physical characteristics, conventional laminotomy leads may require a surgical procedure (a partial laminectomy) for implantation. Multi-column laminotomy leads enable more reliable positioning of a plurality of electrodes as compared to percutaneous leads. Also, laminotomy leads offer a more stable platform that tends to migrate less after implantation and that is capable of being sutured in place. Laminotomy leads also create a uni-directional electrical field and, hence, can be used in a more electrically efficient manner than at least some known percutaneous leads.

Laminotomy leads may be used to apply electrical stimulation to a patient using a plurality of different electrode configurations. To determine which electrode configurations to use for a particular patient, in at least some known neurostimulation systems, mathematical simulations are performed before implanting the lead to predict activation regions. Although the simulations are customized towards the particular patient, they may not accurately reflect the actual response of the patient to electrical stimulation from the implanted lead. Further, after implantation, the lead may migrate, altering the activation regions. Accordingly, it may be relatively difficult for a physician and/or patient to accurately predict and/or determine the actual response to electrical stimulation.

BRIEF SUMMARY OF THE DISCLOSURE

In one embodiment, the present disclosure is directed to a method for monitoring electrical stimulation. The method includes applying electrical stimulation to a patient using a paddle lead that includes a plurality of electrodes, acquiring evoked response data using at least some of the plurality of electrodes, wherein the evoked response data is indicative of a patient response to the electrical stimulation, transmitting the evoked response data to a computing device, and processing the evoked response data using the computing device to facilitate monitoring the applied electrical stimulation.

In another embodiment, the present disclosure is directed to a system for monitoring electrical stimulation. The system includes a paddle lead having a plurality of electrodes, the paddle lead configured to apply electrical stimulation to a patient, and acquire evoked response data using at least some of the plurality of electrodes, wherein the evoked response data is indicative of a patient response to the electrical stimulation. The system further includes a computing device communicatively coupled to the paddle lead, the computing device configured to receive the evoked response data, and process the evoked response data to facilitate monitoring the applied electrical stimulation.

In another embodiment, the present disclosure is directed to a programmer device for programming operation of a paddle lead. The programmer device is configured to receive evoked response data from a paddle lead communicatively coupled to the programmer device, wherein the evoked response data is indicative of a patient response to electrical stimulation applied using the paddle lead, process the evoked response data to facilitate monitoring the applied electrical stimulation.

The foregoing and other aspects, features, details, utilities and advantages of the present disclosure will be apparent from reading the following description and claims, and from reviewing the accompanying drawings.

BRIEF DESCRIPTION OF THE DRAWINGS

FIGS. 5A-5E are schematic diagrams of a paddle stepped through a trolling algorithm in one embodiment.

FIG. 6A is a table of simulation results for operation of a paddle in one embodiment.

Corresponding reference characters indicate corresponding parts throughout the several views of the drawings.

DETAILED DESCRIPTION OF THE DISCLOSURE

Figure 1A:
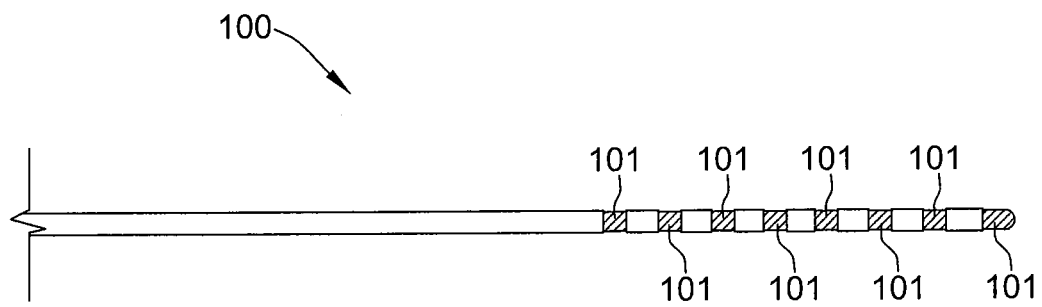
FIG. 1A is a schematic diagram of a conventional percutaneous lead.
Figure 1B:
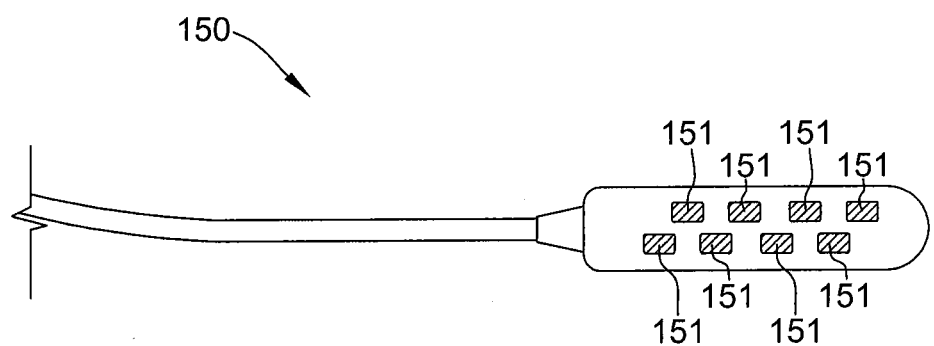
FIG. 1B is a schematic diagram of a conventional paddle lead.

The present disclosure provides systems and methods for monitoring electrical stimulation. A paddle lead includes electrodes capable of both applying electrical stimulation and sensing a patient response to the stimulation. Evoked response data may be processed and/or analyzed by a computing device to modify one or more stimulation parameters and/or detect lead migration.

I. DEFINITIONS

Unless defined otherwise, technical and scientific terms used herein have the same meaning as commonly understood by one of ordinary skill in the art to which this disclosure belongs. For purposes of the present disclosure, the following terms are defined below.

As used herein, the use of the word "a" or "an" when used in conjunction with the term "comprising" in the claims and/or the specification may mean "one", but it is also consistent with the meaning of "one or more," "at least one", and "one or more than one". Still further, the terms "having", "including", "containing" and "comprising" are interchangeable and one of skill in the art is cognizant that these terms are open-ended terms. Some embodiments may consist of or consist essentially of one or more elements, method steps, and/or methods of the disclosure. It is contemplated that any method or composition described herein can be implemented with respect to any other method or composition described herein.

As used herein, the use of the term "dorsal column" refers to conducting pathways in the spinal cord that are located in the dorsal portion of the spinal cord between the posterior horns, and which includes afferent somatosensory neurons. The dorsal column is also known as the posterior funiculus.

As used herein, "spinal cord," "spinal nervous tissue associated with a vertebral segment," "nervous tissue associated with a vertebral segment" or "spinal cord associated with a vertebral segment or level" includes any spinal nervous tissue associated with a vertebral level or segment. Those of skill in the art are aware that the spinal cord and tissue associated therewith are associated with cervical, thoracic and lumbar vertebrae. As used herein, C1 refers to cervical vertebral segment 1, C2 refers to cervical vertebral segment 2, and so on. T1 refers to thoracic vertebral segment 1, T2 refers to thoracic vertebral segment 2, and so on. L1 refers to lumbar vertebral segment 1, L2 refers to lumbar vertebral segment 2, and so on, unless otherwise specifically noted. In certain cases, spinal cord nerve roots leave the bony spine at a vertebral level different from the vertebral segment with which the root is associated. For example, the T1 nerve root leaves the spinal cord myelum at an area located behind vertebral body T8-T9 but leaves the bony spine between T11 and T12.

As used herein the term "chronic pain" refers to a persistent state of pain experienced for a substantial amount of time (e.g., longer than three months).

As used herein the term "complex regional pain syndrome" or "CRPS" refers to painful conditions that usually affect the distal part of an upper or lower extremity and are associated with characteristic clinical phenomena. CRPS is divided into two subtypes CRPS Type I and CRPS Type II. Generally, the clinical characteristics of Type I are the same as seen in Type II. The central difference between Type I and Type II is that Type II typically occurs following a sensory nerve injury whereas Type I occurs in the absence of any known nerve injury.

II. ORGANIZATION OF THE NERVOUS SYSTEM

The nervous system includes two general components, the central nervous system, which is composed of the brain and the spinal cord, and the peripheral nervous system, which is composed of ganglia or dorsal root ganglia and the peripheral nerves that lie outside the brain and the spinal cord. Those of skill in the art will appreciate that the components of the nervous system may be linguistically separated and categorized, but functionally they are interconnected and interactive.

Figure 2:
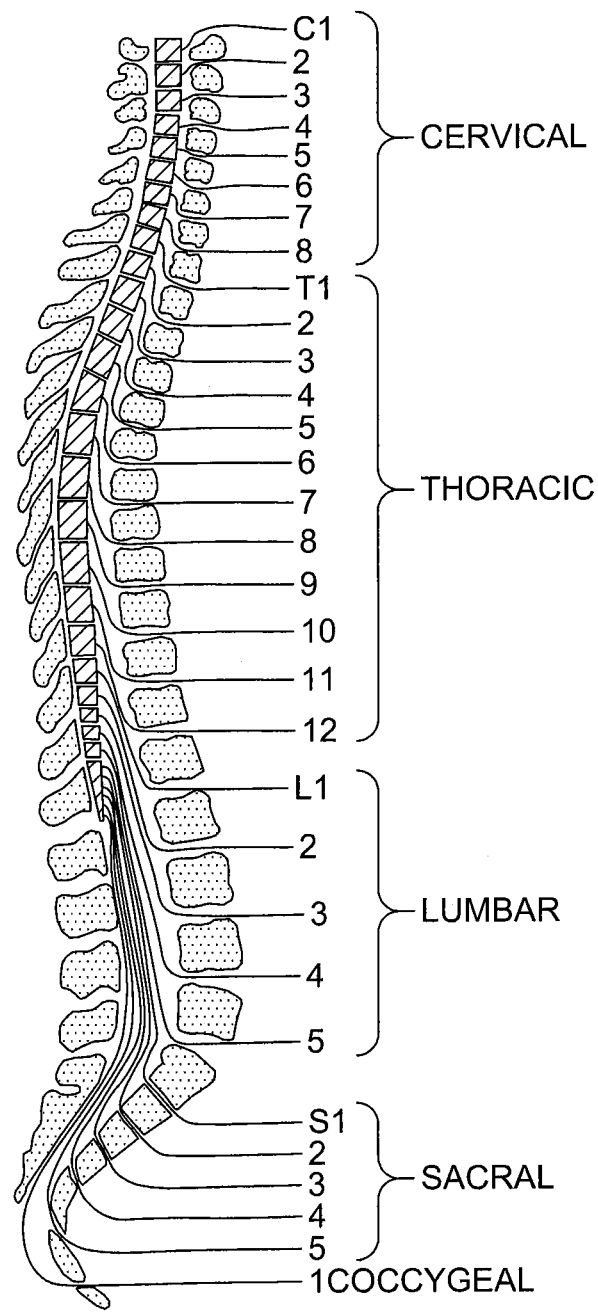
FIG. 2 is a schematic diagram of the spinal cord and the nerve roots in relation to the vertebral spinal canal.

The central nervous system includes the brain and spinal cord, which together function as the principal integrator of sensory input and motor output. In general terms, the brain consists of the cerebrum (cerebral hemispheres and the diencephalons), the brainstem (midbrain, pons, and medulla), and the cerebellum. The spinal cord is organized into segments, for example, there are 8 cervical (C1-C8), 12 thoracic (T1-T12), 5 lumbar (L1-L5), 5 sacral (S1-S5), and 1 cocygeal (Co1) spinal segments. In adults, the spinal cord typically ends at the level of the L1 or L2 vertebral bones. As shown in FIG. 2, the nerve roots travel downward to reach their exit points at the appropriate levels. Left and right sensory and motor nerve roots arise from each segment of the spinal cord except for the C1 and Co1 segments, which have no sensory roots. Associated sensory and motor nerve roots fuse to form a single mixed spinal nerve for each segment. The mixed spinal nerves further fuse and intermingle peripherally to form plexuses and nerve branches.

The peripheral nervous system is divided into the autonomic system (parasympathetic and sympathetic), the somatic system, and the enteric system. The term peripheral nerve is intended to include both motor and sensory neurons and neuronal bundles of the autonomic system, the somatic system, and the enteric system that reside outside of the spinal cord and the brain. Peripheral nerve ganglia and nerves located outside of the brain and spinal cord are also described by the term peripheral nerve.

III. STIMULATION LEADS AND SYSTEMS

Figure 3:
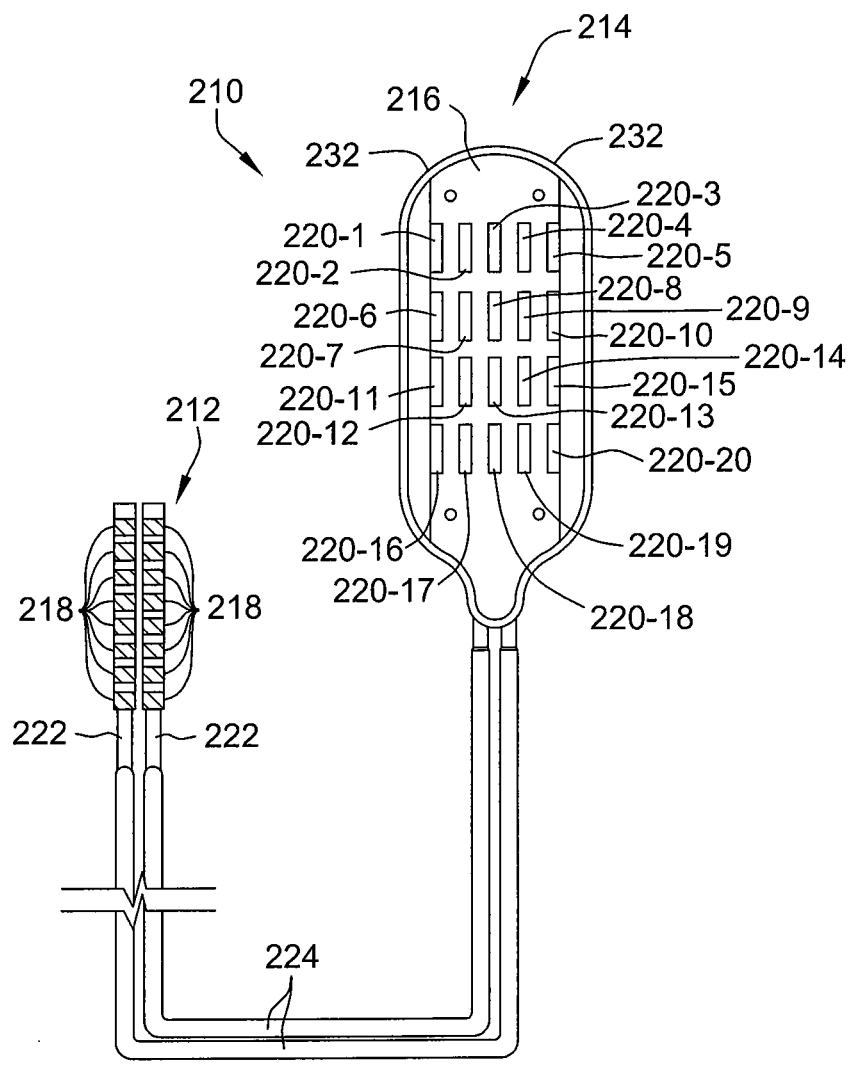
FIG. 3 is a schematic diagram of a paddle lead according to one embodiment.

FIG. 3 is a schematic diagram of a paddle lead 210 according to one embodiment. Paddle lead 210 includes a proximal end 212 and a distal end 214. Proximal end 212 includes a plurality of electrically conductive terminals 218. Distal end 214 includes a plurality of electrically conductive electrodes 220 (labeled 220-1 through 220-20) arranged within a substantially flat, thin paddle 216. Electrodes 220 are mutually separated by insulative material of paddle 216. For a paddle structure adapted for implantation within a cervical vertebral level, electrodes 220 are may be spaced apart 1.5 mm laterally and 2.5 mm longitudinally. For a paddle adapted for implantation within a thoracic vertebral level, electrodes 220 may be spaced apart by 1.0 mm laterally and 2 mm or 3 mm longitudinally. Conductors 222 (which are embedded within the insulative material of the lead body) electrically connect electrodes 220 to terminals 218.

In the embodiment shown in FIG. 3, paddle 216 includes five columns and four rows of electrodes 220 arranged in a grid configuration, for a total of twenty electrodes 220. Alternative numbers of columns and rows may be employed. For example, in some embodiments, thirty-two or more electrodes are distributed into multiple rows and multiple columns. Also, every row need not contain the same number of columns. For example, a number of rows can include a "tripole" design having three columns of electrodes while additional rows can include five or more columns of electrodes to enable a greater amount of electrical field resolution. The multiple columns of electrodes 220 enable lateral control of the applied electrical field to stimulate the exact lateral position of the pertinent nerve fiber(s), as described herein.

Specifically, it may be desirable to selectively stimulate a given dorsal column fiber that is associated with an afflicted region of the patient's body without affecting other regions of the patient's body. The multiple columns of paddles according to representative embodiments provide sufficient resolution to relatively finely control the stimulation of one or several specific fibers, as described herein. Additionally, the multiple columns provide a degree of positional tolerance during the surgical placement of paddle 216 within the epidural space, as any one of the columns may be used to stimulate the pertinent nerve fiber(s). Also, if paddle 216 is displaced relative to the pertinent nerve fibers subsequent to implantation (e.g., due to lead migration), the stimulation pattern applied by a pulse generator can be shifted between columns to compensate for the displacement.

The multiple rows of electrodes 220 enable multiple pain locations to be treated with a single implanted lead. Specifically, a first row can be used to treat a first pain complaint (e.g., pain in the lower extremities) and a second row can be used to treat a second pain location (e.g., post-laminectomy pain in the back). Furthermore, by separating the first and second rows by one or more "buffer" rows of high-impedance electrodes 220, the stimulation in the first and second rows may occur on a substantially independent basis. Specifically, anodes in the second row will have relatively minimal effect on the field distribution generated by cathodes in the first row.

In some embodiments, paddle lead 210 can be implanted within a patient such that electrodes 220 are positioned within the cervical or thoracic spinal levels. After implantation, an electrode combination on a first row of electrodes 220 can be determined that is effective for a first pain location with minimal effects on other regions of the body. The first pain location can be addressed by stimulating a specific dorsal column fiber due to the relatively fine electrical field resolution achievable by the multiple columns. Then, another electrode combination on a second row of electrodes 220 can be determined for a second pain location with minimal effects on other regions of the body. The second pain location could be addressed by stimulating another dorsal column fiber as an example. After the determination of the appropriate electrodes 220 for stimulation, a patient's implantable pulse generator (IPG) can be programmed to deliver pulses using the first and second rows according to the determined electrode combinations.

When determining the appropriate electrode configurations, the selection of electrodes 220 to function as anodes can often facilitate isolation of the applied electrical field to desired fibers and other neural structures. Specifically, the selection of an electrode 220 to function as an anode at a position adjacent to another electrode 220 functioning as a cathode causes the resulting electron/ion flow to be limited to tissues immediately surrounding the two electrodes 220. By alternating through a plurality of anode/cathode combinations, as described herein, it is possible to improve resolution in the stimulation of dorsal column fibers. Also, it is possible to confine the applied electrical field to or away from a periphery of paddle 216.

The operation of anodes can also be used to hyperpolarize neural tissue. Depending on the anode amplitude and the proximity to the pertinent neural tissue, the hyperpolarization can be used to prevent selected neural tissue from propagating action potentials. The hyperpolarization can also be used to prevent an adjacent cathode from initiating propagation of an action potential beginning at the selected neural tissue.

Multiple columns of electrodes 220 also enable lateral "steering" of the electrical field using a single channel pulse generator. A single channel pulse generator refers to a pulse generator that provides an equal magnitude pulse to each active electrode 220 at a given time. Specifically, each electrode 220 is either "active" (i.e., it is coupled to the pulse generator output during pulse generation by a suitable gate or switch) or "inactive" (i.e., the gate or switch does not couple the electrode to the pulse generator output). Each "active" electrode 220 experiences the same amplitude; only the polarity varies depending upon whether electrode 220 is set as a cathode or anode as defined by positions of respective gates and/or switches.

The steering of the electrical field occurs by selecting appropriate states for electrodes 220. Depending upon the desired neural tissue to be stimulated, it may be beneficial to confine the electrical field along the periphery of paddle 216. Confinement of the electrical field along the periphery can be accomplished by setting electrode 220-1 to function as a cathode and setting electrode 220-2 to function as an anode. Because the electrical field will generally be confined between these two electrodes 220 during stimulation pulses, only nerve fibers within the adjacent area will be stimulated. Generally speaking, nerve fibers past electrode 220-2 would not be stimulated when a pulse is delivered via electrode 220-1 due to the anodal blocking.

Conductors 222 are carried in sheaths 224. In some embodiments, each sheath 224 carries eight conductors 222. With only two sheaths 224 with eight conductors each, there would only be sixteen conductors 222. To accommodate the lower number of conductors 222 than electrodes 220, multiple electrodes 220 may be coupled to the same conductor 222 (and, hence, to a common terminal 218). In the example embodiment, electrodes 220-1 and 220-6 are coupled to a common conductor 222, electrodes 220-5 and 220-10 are coupled to a common conductor 222, electrodes 220-11 and 220-16 are coupled to a common conductor, and electrodes 220-15 and 220-20 are coupled to a common conductor. Electrodes 220-2 through 220-4, 220-7 through 220-9, 220-12 through 220-14, and 220-17 through 220-19 are each independently coupled to their own respective conductor 222.

In some embodiments, other electrode designs can be employed to minimize the number of conductors 222 required to support the various electrodes 220. For example, a relatively large number of electrodes 220 (e.g., thirty-two, sixty-four, and greater) could be utilized on paddle 216. Electrodes 220 could be coupled to one or several electrical gates (e.g., as deposited on a flex circuit). The electrical gates can be controllably configured to couple each electrode 220 to a conductor 222 carrying cathode pulses, to couple each electrode 220 to an anode termination, or to maintain each electrode 220 at a high impedance state. The electrical gates could be controlled using a main controller, such as a logic circuit, on the paddle 216 that is coupled to a data line conductor 222. The data line conductor 222 communicates signals from an IPG that identify the desired electrode states, and the main controller responds to the signals by setting the states of the electrical gates as appropriate.

In another embodiment, a cathode conductor line 222 and an anode conductor line 222 are provided in one or several lead bodies along with a plurality of optical fibers. The optical fibers are used to carry optical control signals that control the electrode states. Specifically, paddle 216 includes photodetectors (e.g., photodiodes) that gate connections to anode conductor line 222 and cathode conductor line 222. The use of optical fibers to carry optical control signals may be advantageous, because the diameter of optical fibers suitable for such functionality is smaller than electrical conductors 222. Therefore, a larger number of electrodes 220 (as compared to using a separate electrical conductor 222 for each electrode 220) can be independently controlled while maintaining the lead body diameters at an acceptable size.

Terminals 218 and electrodes 220 are preferably formed of a non-corrosive, highly conductive material. Examples of such material include stainless steel, MP35N, platinum, and platinum alloys. In one embodiment, terminals 218 and electrodes 220 are formed of a platinum-iridium alloy. Each conductor 222 is formed of a conductive material that exhibits desired mechanical properties of low resistance, corrosion resistance, flexibility, and strength. While conventional stranded bundles of stainless steel, MP35N, platinum, platinum-iridium alloy, drawn-brazed silver (DBS) or the like can be used, one embodiment uses conductors 222 formed of multi-strands of drawn-filled tubes (DFT). Each strand is formed of a low resistance material and is encased in a high strength material (preferably, metal). A selected number of "sub-strands" are wound and coated with an insulative material. With regard to the operating environment of representative embodiments, such insulative material protects an individual conductor 222 if its respective sheath 224 is breached during use.

In addition to providing the requisite strength, flexibility, and resistance to fatigue, conductors 222 formed of multi-strands of drawn-filled tubes, in accordance with the above description, provide a low resistance alternative to other materials. Specifically, a stranded wire, or even a coiled wire, of approximately 60 cm and formed of MP35N or stainless steel or the like may have a measured resistance in excess of 30 ohms. In contrast, for the same length, a wire formed of multi-strands of drawn-filled tubes could have a resistance less than 4 ohms.

Sheaths 224 and paddle 216 are preferably formed from a medical grade, substantially inert material, for example, polyurethane, silicone, or the like. Importantly, such material should be non-reactive to the environment of the human body, provide a flexible and durable (i.e., fatigue resistant) exterior structure for the components of paddle lead 210, and insulate adjacent terminals 218 and/or electrodes 220. Additional structure (e.g., a nylon mesh, a fiberglass substrate) (not shown) can be internalized within paddle 216 to increase its overall rigidity and/or to cause paddle 216 to assume a prescribed cross-sectional form.

Paddle 216 may be fabricated to possess a substantially flat profile. Alternatively, paddle 216 may have an arcuate profile. In the embodiment shown in FIG. 3, wing structures 232 are formed on each longitudinal side of paddle 216. Wing structures 232 may be formed for the purpose of retaining paddle 216 within the central portion of the epidural space. In some embodiments, one or more electrodes 220 may be disposed on wing structures 232.

While a number of material and construction options have been discussed above, it should be noted that neither the materials selected nor the construction methodology is critical to the systems and methods described herein.

Figure 4:
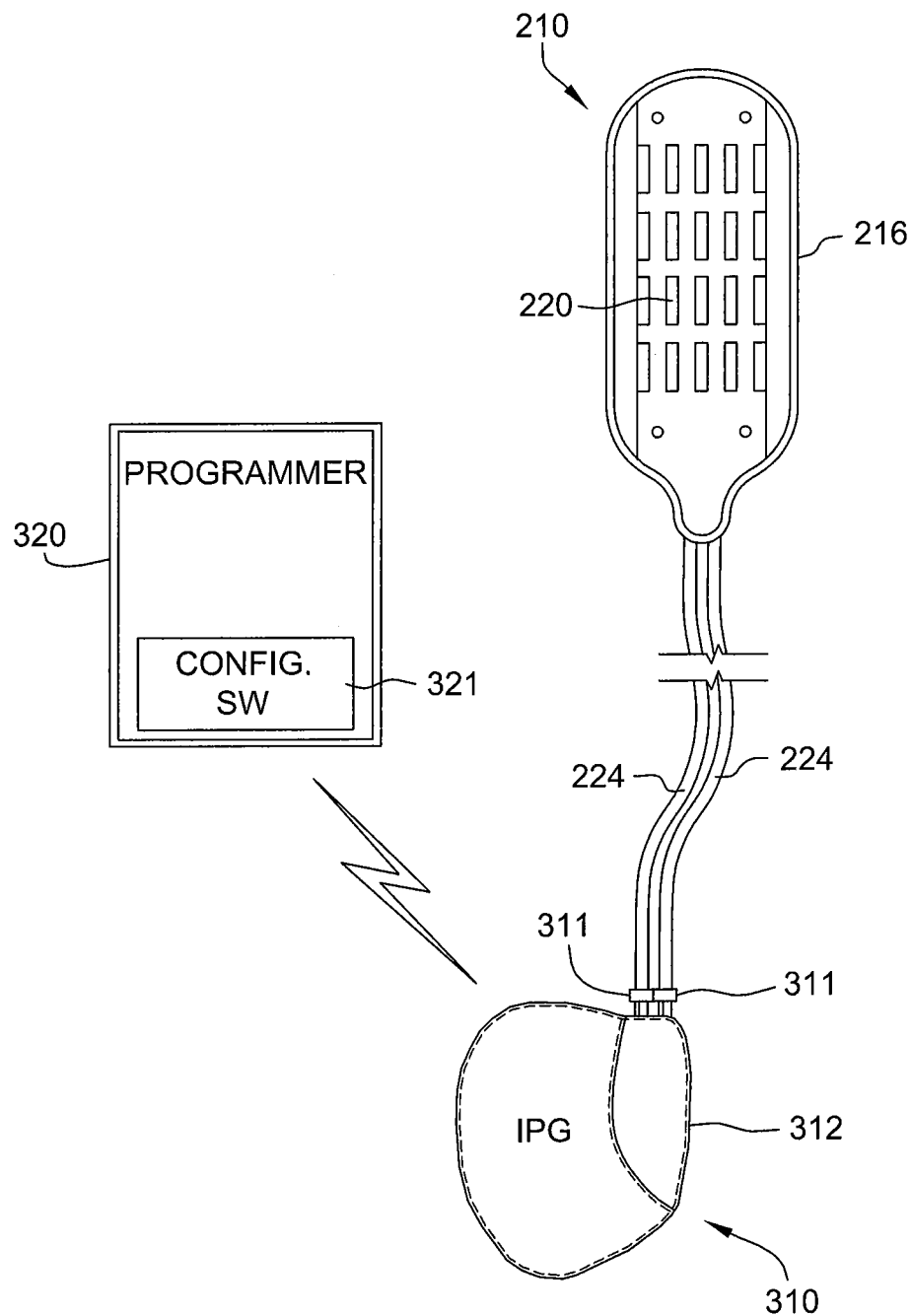
FIG. 4 is a schematic diagram of a paddle lead coupled to an implantable pulse generator in communication with a wireless programmer device according to one embodiment.

FIG. 4 depicts paddle lead 210 coupled to an IPG 310 which is in wireless communication with a programmer device 320. An example of a commercially available IPG is the Eon™ Rechargeable IPG from St. Jude Medical, Inc. (Plano, Tex.), although any suitable IPG, such as RF powered devices, could be alternatively employed. As shown in FIG. 4, paddle lead 210 is coupled to header ports 311 of IPG 310. Each header port 311 electrically couples respective terminals 218 (shown in FIG. 3) to a switch matrix (not shown) within IPG 310.

The switch matrix selectively connects the pulse generating circuitry (not shown) of IPG 310 to terminals 218, and, hence to electrodes 220. A sealed portion 312 of IPG 310 contains pulse generating circuitry, communication circuitry, control circuitry, and a battery (not shown) within an enclosure to protect the components after implantation within a patient. The control circuitry may comprise a microprocessor, one or more ASICs, and/or any suitable circuitry for controlling the pulse generating circuitry. The control circuitry controls the pulse generating circuitry to apply electrical pulses to the patient via electrodes 220 of paddle 216 according to multiple pulse parameters (e.g., pulse amplitude, pulse width, pulse frequency, etc.). Electrodes 220 are set to function as cathodes or anodes or set to a high-impedance state for a given pulse according to the couplings provided by the switch matrix. The electrode states may be changed between pulses.

When paddle lead 210 is initially implanted within the patient, a determination of the set(s) of pulse parameters and the electrode configuration(s) that may effectively treat the patient's condition is made. The determination or programming typically occurs through a physician's interaction with configuration software 321 executed on programmer device 320. Configuration software 321 steps the physician through a number of parameters and electrode configurations based on a trolling algorithm. In some embodiments, the electrode configurations are stepped through by laterally "steering" the electrical field by moving the anodes and/or cathodes along a row of the paddle. The patient provides feedback to the physician regarding the perceived stimulation that occurs in response the pulse parameters and electrode configuration(s). The physician may effect changes to the parameters and electrode configuration(s) until optimal pulse parameters and electrode configuration(s) are determined. The final pulse parameters and configurations are stored within IPG 310 for subsequent use. The pulse parameters and configurations are used by IPG 310 to control the electrical stimulation provided to the patient via paddle lead 210. Although single channel IPGs have been described according to some embodiments, multiple current or voltage source IPGs could alternatively be employed.

FIGS. 5A-5E are schematic diagrams of paddle 216 stepped through a trolling algorithm in one embodiment. The trolling algorithm may be executed using, for example programmer device 320. Specifically, in the embodiment shown in FIGS. 5A-5E, paddle 216 is selectively stepped through five different states (e.g., a first state shown in FIG. 5A, a second state shown in FIG. 5B, etc.). In at least some conventional trolling algorithms, a paddle lead is configured to be stepped through thirteen separate states. Accordingly, the trolling algorithm demonstrated in FIGS. 5A-5E includes significantly less states than at least some conventional trolling algorithms, reducing the programming needed to perform the algorithm.

Paddle 216 may switch from state to state in response to a user input (e.g., using programmer device 320), or alternatively, may cycle through the states at a predetermined frequency. When a selected state applies focused stimulation to a desired nerve, paddle 216 may be held in that state. Accordingly, by selectively stepping through the different states (e.g., using IPG 310 and/or programmer device 320), the location to which an electric field is applied can be controlled.

As paddle 216 is stepped through the different states, electrodes 220 that function as cathodes gradually move from left to right. Specifically, in the first state (FIG. 5A), electrode 220-7 functions as a cathode, in the second state (FIG. 5B), electrodes 220-7 and 220-8 function as cathodes, in the third state (FIG. 5C), electrode 220-8 functions as a cathode, in the fourth state (FIG. 5D), electrodes 220-8 and 220-9 function as cathodes, and in the fifth state (FIG. 5E), electrode 220-9 functions as a cathode. Because the cathodes are gradually moved from left to right, the coverage range across the five states hits substantially every nerve without gaps in dermatome zones.

Figure 6B:
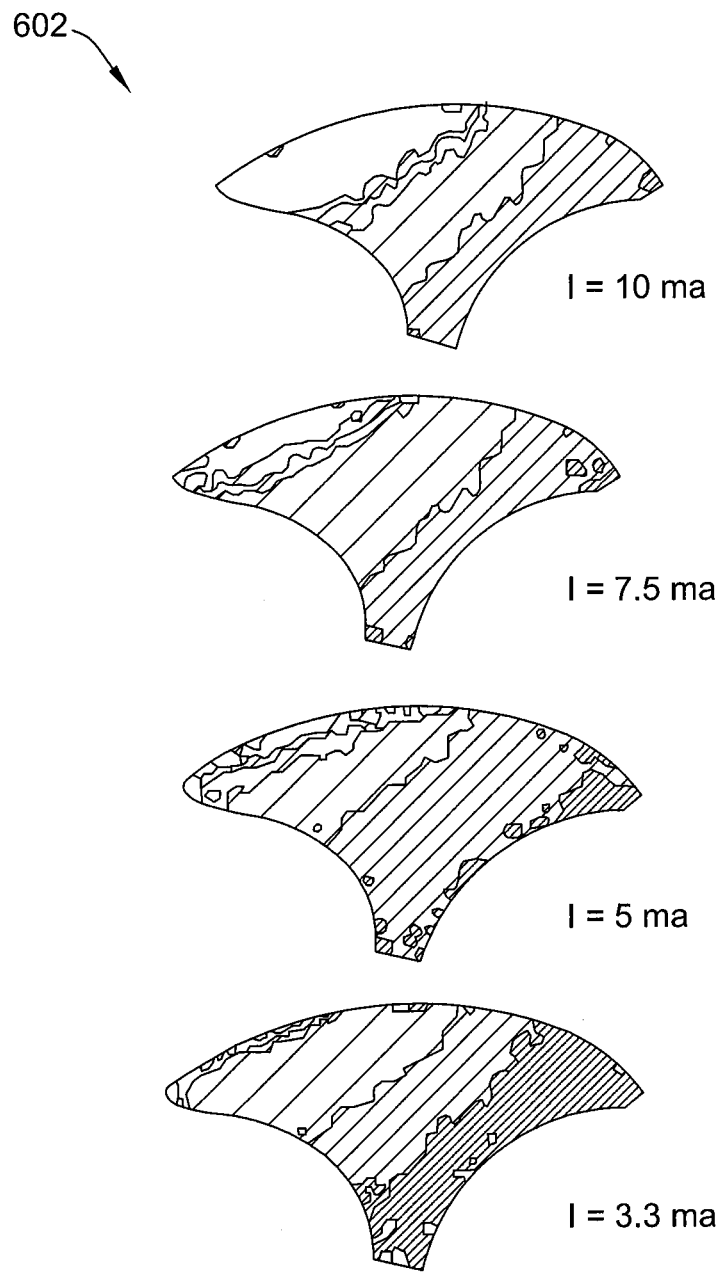
FIG. 6B is a set of diagrams schematically mapping the results in the table shown in FIG. 6A to dermatome zones.

Notably, each state shown in FIGS. 5A-5E includes guarding anodes to the left and right of the one or more cathodes in the same row as the one or more cathodes. As compared to at least some known electrode configurations, the guarding anodes facilitate improving a localization (i.e., focus) of electrical simulation performed using paddle 216. Specifically, the guarding anodes facilitate containing generated electric fields. For example, simulation of electrical stimulation from the first state (FIG. 5A) was performed using finite element analysis. FIG. 6A is a table 600 of the results of the simulation, and FIG. 6B is a set 602 of diagrams schematically mapping the results in table 600 to dermatome zones. As demonstrated by FIGS. 6A and 6B, even at relatively high input currents (e.g., 10 milliamps (mA)), the electrical stimulation to dermatome zones is relatively localized, and substantially limited to a left side.

Figure 7:
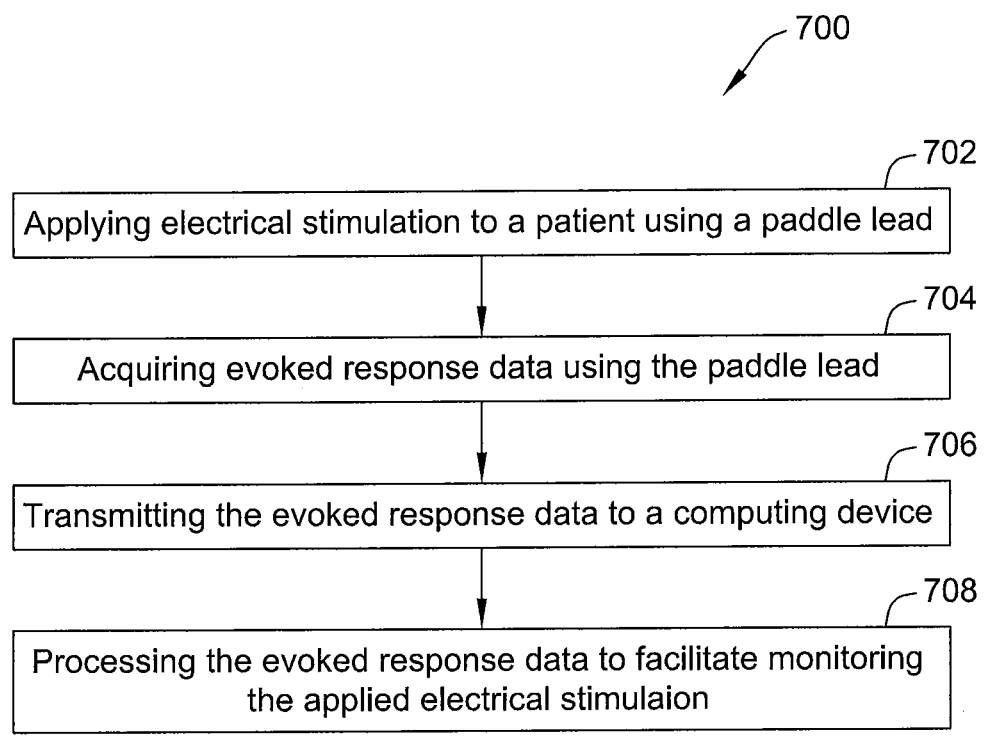
FIG. 7 is a flow chart of one embodiment of a method for monitoring electrical stimulation.

In some embodiments, paddle 216 is used to sense an evoked response generated by electrical stimulation applied to the patient to monitor the electrical stimulation. FIG. 7 is a flow chart of one embodiment of a method 700 for monitoring electrical stimulation. At block 702, electrical stimulation is applied to a patient using paddle lead 210. At block 704, evoked response data is acquired using paddle lead 210. The evoked response data is transmitted to a computing device (e.g., programmer device 320 or IPG 310) at block 706. At block 708, the evoked response data is processed by the computing device to facilitate monitoring the applied electrical stimulation.

The evoked response data may be processed to guide programming of paddle lead 210, as described in detail herein. For example, the evoked response data may be solved inversely to map the stimulation and generate an activation map, similar to the mapping shown in FIG. 6B.

In one embodiment, evoked response data is acquired immediately after delivering stimulation pulses using paddle 216. Specifically, electrodes 220 acquire voltage measurements indicative of evoked response compound action potentials (ECAP) after stimulation is applied. In this embodiment, every electrode 220 acquires a voltage measurement. Accordingly, paddle 216 acquires sixteen separate voltage measurements in this embodiment (i.e., from the twelve independent electrodes 220 and the four pairs of linked electrodes 220). Alternatively, any number of electrodes 220 (i.e., less than all) may be used to acquire voltage measurements.

In this embodiment, voltage measurements are acquired over a period of 4 milliseconds (ms) after stimulation is applied. Alternatively, voltage measurements may be acquired over any period of time that enables paddle 216 to function as described herein. The acquired voltage measurements may be stored, for example, on IPG 310 and/or programmer device 320.

The acquired voltage measurements may be displayed to a user, for example, on a display module (e.g., an LCD display) of programmer device 320. For example, programmer device 320 may display a map of sensed voltages at a particular instance between 1 and 2 ms after stimulation. Further, programmer device 320 may display an activation map generated by inversely solving the acquired voltage measurements, as described below.

In some embodiments, programmer device 320 displays a voltage map for one electrode 220 over a period of time. In other embodiments, programmer device 320 displays a voltage map for all electrodes 220 at a particular instance. When the voltage map includes voltages for one electrode 220 over a period of time, programmer device 320 may record a peak value of the voltage. The peak value may be detected, for example, using a peak detection software and/or hardware.

The voltage measurements may be acquired and recorded using any suitable techniques. In one embodiment, paddle 216 acquires voltage measurements daily at one or more scheduled times (e.g., during the night). In some embodiments, IPG 310 includes a three-dimensional accelerometer that enables the acquired voltages to be associated with a detected posture of the patient. Detecting posture changes in some locations (e.g., the buttock) may be relatively difficult, but positional changes may still be detectable.

As described above, in some embodiments, all electrodes 220 on paddle 216 acquire voltage measurements. Evoked response data may be collected for each electrode 220 over predetermined time windows (e.g., 4 ms) for a predetermined number of pulses (e.g., 10-20 pulses). This may be repeated for a plurality of stimulation configurations, such as each of the five configurations shown in FIGS. 5A-5E.

In one embodiment, the evoked response data (i.e., the acquired voltage measurements) is transmitted, or uploaded, to programmer device 320. For each stimulation configuration, programmer device 320 processes the evoked response data to create a sensed voltage map. Programmer device 320 may process the evoked response data once daily, or multiple times per day. In one embodiment, the sensed voltage map is generated for a predetermined time that falls between 1 and 2 ms after stimulation. Alternatively, the sensed voltage map may be generated at any suitable time and/or during any suitable time period. This process is repeated for each stimulation configuration, and sensed voltage maps are created for each stimulation configuration.

Figure 8:
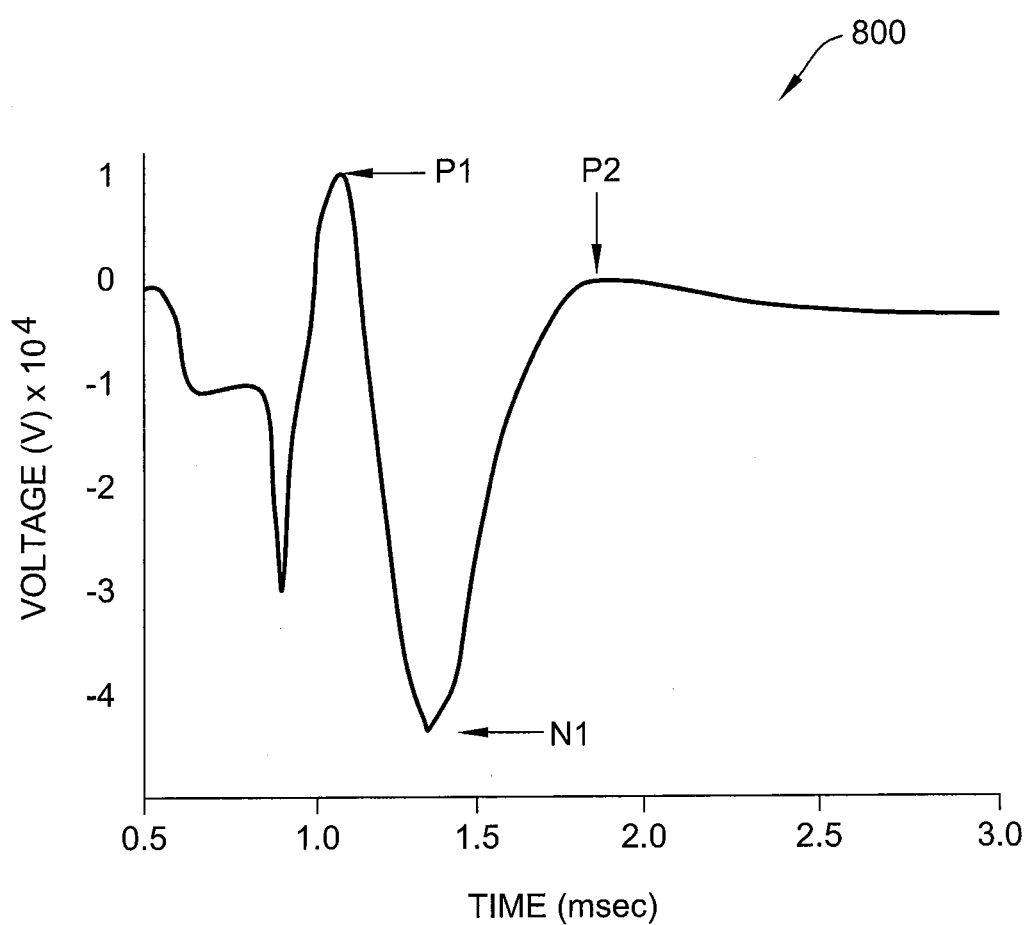
FIG. 8 is an example of a sensed voltage map in one embodiment.

FIG. 8 is an example of a sensed voltage map 800 for a single electrode 220. Sensed voltage map 800 may be displayed, for example, on programmer device 320. As shown in FIG. 8, between 1 and 2 ms after stimulation, sensed voltage map 800 includes a first peak, P1, a first nadir, N1, and a second peak P2. Programmer device 320 may calculate a peak to peak difference between first peak P1 and first nadir N1, or between first nadir N1 and second peak P2. This calculation may be repeated for some or all other electrodes 220 on paddle 216. Further, the calculated values may be used to determine lead migration, as described below in reference to FIG. 9.

Based on the evoked response data and/or any sensed voltage maps, inverse modeling algorithms are utilized to calculate activation regions in the dorsal column of the patient. As hand-held electronic devices may include sufficient memory to perform the inverse modeling, the inverse modeling may be performed, for example, using programmer device 320. An image illustrating the activation regions may be displayed to a user, for example, using programmer device 320. The image may have the same depiction as the diagrams in FIG. 6B, for example.

The sensed voltage maps and/or inversely calculated activation regions may be used by a physician to monitor and/or adjust the stimulation applied by paddle 216. For example, from the sensed voltage maps and/or inversely calculated activation regions, the physician may verify whether a selected stimulation configuration is effectively applying stimulation to the patient. Based on the sensed voltage maps and/or inversely calculated activation regions, the physician may choose to adjust one or more programming parameters (e.g., pulse width, frequency, amplitude) using, for example, programmer device 320. Accordingly, processing the evoked response data provides valuable feedback to the physician, facilitating improved treatment of the patient.

The sensed voltage maps and/or inversely calculated activation regions may also be employed to determine whether lead migration has occurred. That is, if paddle lead 210 shifts, or migrates, substantially, the sensed voltage maps and/or inversely calculated activation regions should also change substantially. Accordingly, in one embodiment, a computing device (e.g., programmer device 320 and/or IPG 310) compares current sensed voltage maps and/or inversely calculated activation regions with previous sensed voltage maps and/or inversely calculated activation regions to determine whether significant changes have occurred.

For example, a difference between the previous sensed voltage maps and/or inversely calculated activation regions and the current sensed voltage maps and/or inversely calculated activation regions may be compared to a predetermined threshold. In one embodiment, if the difference is greater than the predetermined threshold, programmer devices 320 generates an audio and/or visual alert to notify the patient or physician of the potential lead migration. For example, programmer device 320 may display a warning or emit an audible alarm. Further, because the sensed voltage maps are associated with a particular stimulation configuration, programmer device 320 may also indicate the location of the potential lead migration. That is, programmer device 320 may indicate (visually or audibly) the electrode 220 near which the potential lead migration occurred.

Figure 9:
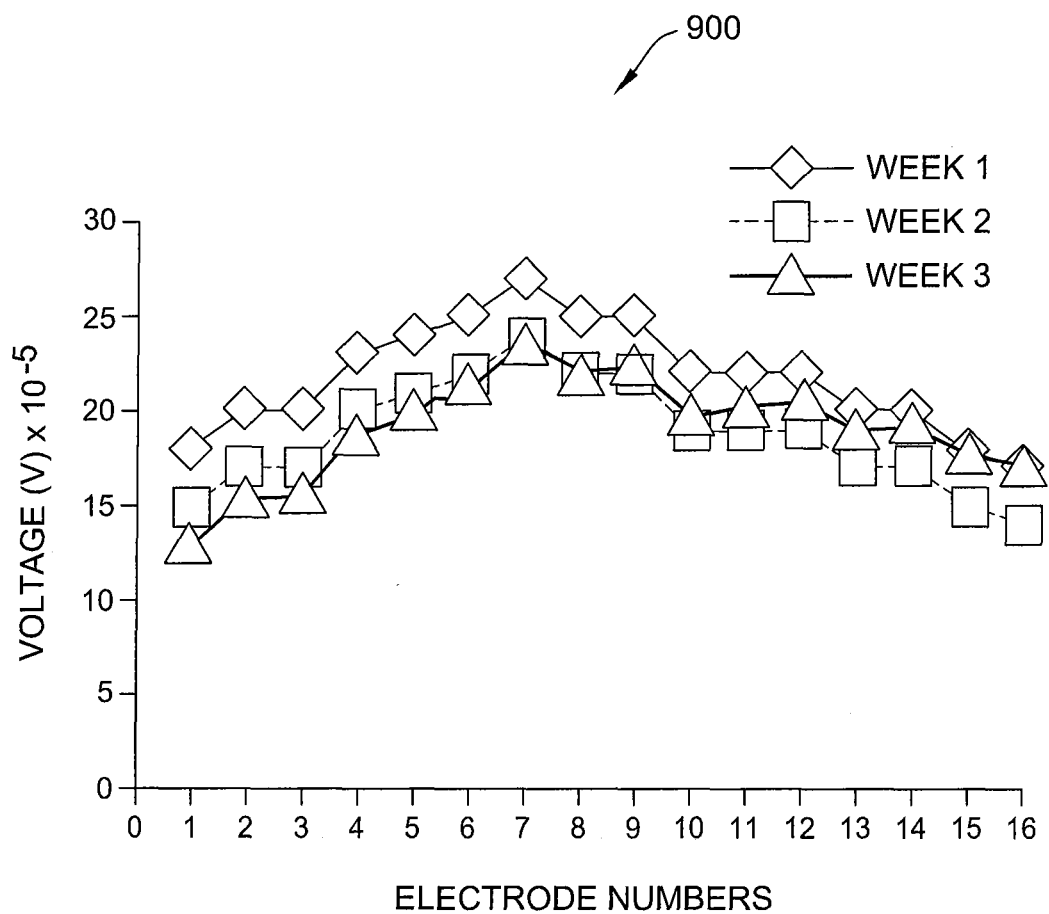
FIG. 9 is an example of a graph illustrating changes in sensed voltage over time.

As noted above, in some embodiments, programmer device 320 may use calculated peak to peak values to detect lead migration over time. FIG. 9 is an example of a graph 900 illustrating changes in sensed voltage over time. More specifically, graph 900 shows the peak to peak difference between a first peak P1 and a first nadir N1 for sixteen different electrodes, taken at three different points in time (i.e., week 1, week 2, and week 3). Graph 900 may be displayed, for example, on programmer device 320.

As demonstrated by FIG. 9, graph 900 enables detection of lead migration. For example, between week 1 and week 2, the change in the voltage curve indicates that paddle lead 210 has shifted away from the corticospinal tract (CST) of the subject (e.g., by approximately 1 millimeter). Further, the change in the voltage curve between week 2 and week 3 indicates that the paddle lead 210 has rotated. The processed information (e.g., the data in graph 900) may be utilized by simulations to predict possible future lead migration. Moreover, in some embodiments, programmer device 320 may provide these predictions to a user (e.g., by displaying them) and/or may provide, to the user, suggested stimulation modifications (e.g., suggested stimulation configurations) to address the predicted migrations.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A method for monitoring electrical stimulation, the method comprising:
    applying electrical stimulation to a patient using a paddle lead that includes a plurality of electrodes;

acquiring evoked response data using at least some of the plurality of electrodes, wherein the evoked response data is indicative of a patient response to the electrical stimulation;

transmitting the evoked response data to a computing device; and processing the evoked response data using the computing device to facilitate monitoring the applied electrical stimulation, wherein processing the evoked response data comprises utilizing inverse modeling algorithms to determine at least one application region for the electrical stimulation.

2. The method of claim 1, wherein acquiring evoked response data comprises acquiring voltage measurements.

3. The method of claim 1, wherein acquiring evoked response data comprises acquiring evoked response data using all of the plurality of electrodes.

4. The method of claim 1, wherein processing the evoked response data comprises processing the evoked response data using a programming device configured to program operation of the paddle lead.

5. The method of claim 1, wherein processing the evoked response data comprises generating at least one voltage map.

6. The method of claim 5, wherein generating at least one voltage map comprises generating at least one voltage map that illustrates a measured voltage for a plurality of electrodes at a predetermined point in time.

7. The method of claim 5, wherein generating at least one voltage map comprises generating at least one voltage map that illustrates a measured voltage over a period of time for one electrode of the plurality of electrodes.

8. The method of claim 1, further comprising:

comparing the evoked response data to previously acquired evoked response data; and determining, based on the comparison, whether migration of the paddle lead has occurred.

9. A system for monitoring electrical stimulation, the system comprising:

a paddle lead comprising a plurality of electrodes, the paddle lead configured to:

apply electrical stimulation to a patient; and acquire evoked response data using at least some of the plurality of electrodes, wherein the evoked response data is indicative of a patient response to the electrical stimulation; and a computing device communicatively coupled to the paddle lead, the computing device configured to:

receive the evoked response data; and process the evoked response data to facilitate monitoring the applied electrical stimulation, wherein to process the evoked response data, the computing device is configured to utilize inverse modeling algorithms to determine at least one application region for the electrical stimulation.

10. The system of claim 9, wherein to acquire evoked response data, the paddle lead is configured to acquire voltage measurements.

11. The system of claim 9, wherein to acquire evoked response data, the paddle lead is configured to acquire evoked response data using all of the plurality of electrodes.

12. The system of claim 9, wherein the computing device comprises a programming device configured to program operation of the paddle lead.

13. The system of claim 9, wherein to process the evoked response data, the computing device is configured to generate at least one voltage map.

14. The system of claim 9, wherein the computing device is further configured to:

compare the evoked response data to previously acquired evoked response data; and determine, based on the comparison, whether migration of the paddle lead has occurred.

15. A programmer device for programming operation of a paddle lead, the programmer device configured to:

receive evoked response data from a paddle lead communicatively coupled to the programmer device, wherein the evoked response data is indicative of a patient response to electrical stimulation applied using the paddle lead; and process the evoked response data to facilitate monitoring the applied electrical stimulation, wherein to process the evoked response data, the programmer device is configured to utilize inverse modeling algorithms to determine at least one application region for the electrical stimulation.

16. The programmer device of claim 15, wherein to process the evoked response data, the programmer device is configured to:

generate at least one voltage map; and display the at least one voltage map to a user.

17. The programmer device of claim 15, wherein the programmer device is further configured to: compare the evoked response data to previously acquired evoked response data; and generate an alert when the comparison indicates that migration of the paddle lead has occurred.

* * * * *